United States Patent [19]

Kamaga

[11] Patent Number: 5,090,433
[45] Date of Patent: Feb. 25, 1992

[54] COMPACT ENDOSCOPE CLEANING APPARATUS

[75] Inventor: Ryuichi Kamaga, Utsunomiya, Japan

[73] Assignee: Kabushiki Kaisha Toshiba, Kawasaki, Japan

[21] Appl. No.: 302,959

[22] Filed: Jan. 30, 1989

[30] Foreign Application Priority Data

Jan. 28, 1988 [JP] Japan .................................. 63-15909

[51] Int. Cl.⁵ .............................................. B08B 3/04
[52] U.S. Cl. .................................. 134/169 C; 134/200; 134/182; 15/21.1
[58] Field of Search ........... 134/166 R, 166 C, 169 R, 134/169 C, 200, 182, 92, 84, 900; 15/21 E, 88, 104.04

[56] References Cited

U.S. PATENT DOCUMENTS

| | | | |
|---|---|---|---|
| 946,370 | 1/1910 | Kelmel | 15/88 |
| 981,417 | 1/1911 | Halsey et al. | 15/88 X |
| 1,511,825 | 10/1924 | Burns | 134/200 |
| 2,960,706 | 11/1960 | Dunham | 15/104.04 X |
| 3,009,408 | 11/1961 | Eberle | 134/200 X |
| 3,879,787 | 4/1975 | Russo | 134/200 X |
| 3,963,438 | 6/1976 | Banez | 134/168 C |
| 4,125,087 | 11/1978 | Ronning | 15/104.04 X |
| 4,130,124 | 12/1978 | Sherwin | 134/138 |
| 4,281,674 | 8/1981 | Tanaka et al. | 134/170 X |
| 4,288,882 | 9/1981 | Takeuchi | 15/88 |
| 4,299,244 | 11/1981 | Hirai | 134/170 X |
| 4,336,816 | 6/1982 | Horz et al. | 134/188 |
| 4,748,007 | 5/1988 | Gaudion et al. | 134/170 |
| 4,750,230 | 6/1988 | Osborn | 15/104.04 X |

FOREIGN PATENT DOCUMENTS

| | | | |
|---|---|---|---|
| 2396443 | 3/1975 | France | 15/88 |
| 60-122101 | 8/1985 | Japan . | |

*Primary Examiner*—Frankie L. Stinson
*Attorney, Agent, or Firm*—Foley & Lardner

[57] ABSTRACT

A cleaning apparatus is used for cleaning a scope of an endoscope after completing medical inspection by the endoscope. The cleaning apparatus has a cylindrical cleaning vessel. This cylindrical cleaning vessel includes top and bottom portions, a scope insertion hole formed in the top portion, and a cleaning-fluid conducting hole formed in the bottom portion. This cylindrical cleaning vessel is detachably mounted on a rod of a scope stand.

4 Claims, 5 Drawing Sheets

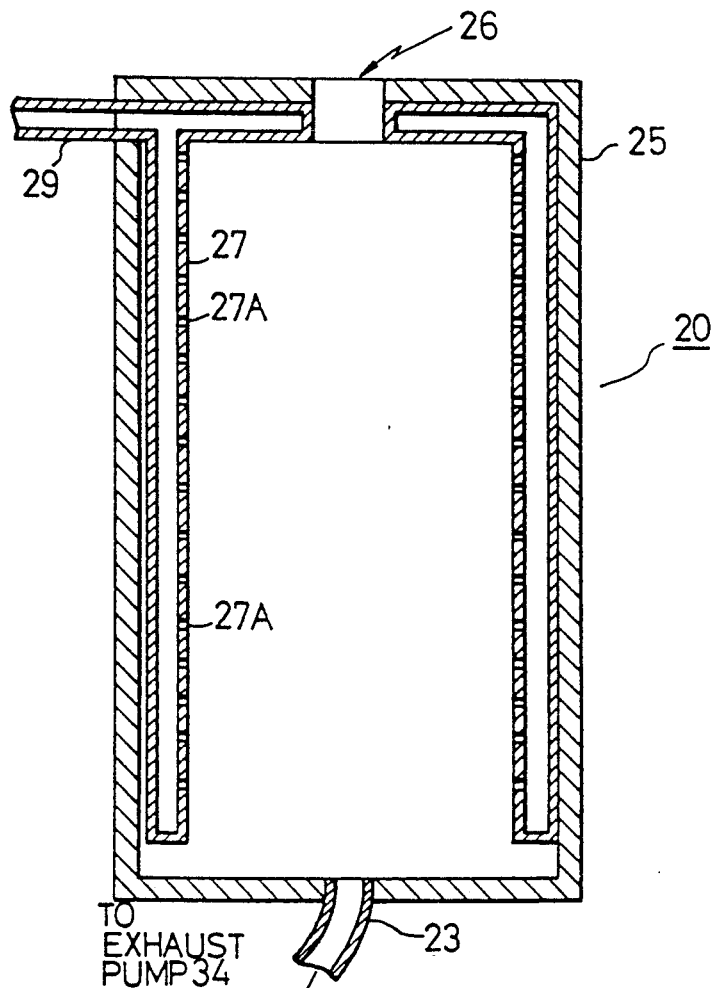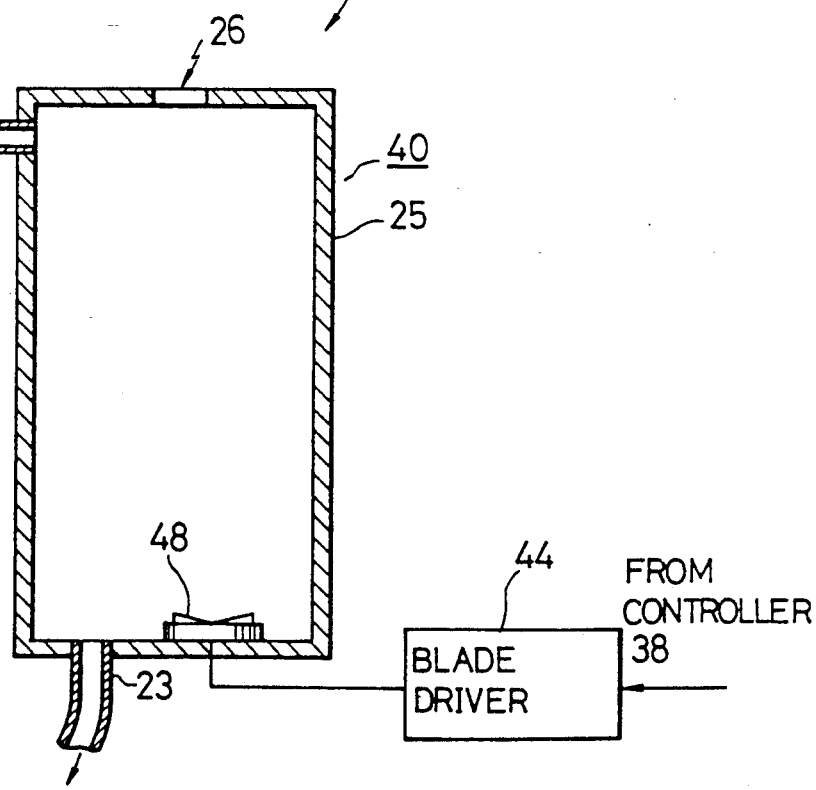

COMPACT ENDOSCOPE CLEANING APPARATUS

BACKGROUND OF THE INVENTION

1. Field of the Invention

The present invention generally relates to an endoscope cleaning apparatus. More particularly, the present invention is directed to an endoscope cleaning apparatus capable of simply cleaning a scope of an endoscope.

2. Description of the Related Art

In, for instance, a medical inspection room employing an endoscope, the conventional endoscope cleaning apparatus is installed under such a condition that no specific intention is paid in a relationship between the suspended positions of scopes of these endoscopes and the install position of the cleaning apparatus. In other words, the position at which the scope of the endoscope used in the medical endoscope inspection is suspended on the endoscope stand, is apart from the position at which the cleaning apparatus is installed within the medical inspection room.

In use of such a commercially available endoscope cleaning apparatus, all of the endoscopes which have been used for the medical endoscope inspection in, for instance, a day are cleaned after completion of the medical endoscope inspection. In other words, if the scheduled medical endoscope inspection is not yet accomplished, usually the cleaning operation of the endoscopes used in this inspection is not carried out.

In a practical case, needs are however made to clean the used scopes of the endoscopes even during the medical endoscope inspection. In such a case, the used scopes of the endoscopes are cleaned under the suspended condition on the scope stand not by using the conventional endoscope cleaning apparatus, but simply by using a gauze wetted with cleaning fluid. Otherwise these used scopes are manually washed by use of water.

The above-described conventional manual cleaning operations by wiping the used scope by the gauze wetted with the cleaning fluid, or the water, require a plenty of cleaning operation time, and cumbersome works. When the used scope is manually washed by way of water for the cleaning purpose, the cleaning water may be dispersed which causes medical dirty problems. In general, there is no cleaning tub in an endoscope medical inspection room. Even if such a cleaning tub for medical tools is employed, it is generally positioned far from an inspection bed site where an endoscope is installed, so that this endoscope must be picked-up from the scope stand and thereafter be moved to the cleaning tub positioned far from the endoscooe stand. As a result, such conventional manual-cleaning operations provide various problems in view of the medical inspection and endoscope operabilities.

On the other hand, to accomplish the medical endoscope inspection as quickly as possible, the time required for cleaning the used scope must be shortened in view of the medical conditions of a biological body under examination.

As a consequence, the cleaning operation for the used scopes of the endoscopes is normally commenced after the medical endoscope inspection of the biological body has been completely accomplished.

SUMMARY OF THE INVENTION

The present invention has been made in an attemt to solve the various problems caused by the conventional scope cleaning operations, and has an object to provide an endoscope cleaning apparatus capable of simply cleaning the used scopes of the endoscopes even during the medical endoscope inspection.

An endoscope cleaning apparatus according to the invention, comprises:

an elongated cleaning vessel including;

a top portion and a bottom portion positioned opposite to each other along a longitudinal axis thereof;

a scope insertion hole formed in the top portion, through which the scope of the endoscope is insertable, whereby a substantially entire length of the scope is stored within said elongated cleaning vessel in a vertical direction parallel to the longitudinal direction;

a cleaning-fluid conducting hole formed in a first portion adjacent to the top portion, through which cleaning fluid is conducted into the elongated cleaning vessel; and, an exhaust hole formed in a second portion adjacent to the bottom portion, through which the effluent of the cleaning fluid is exhausted from the elongated cleaning vessel.

According to the endoscope cleaning apparatus of the present invention, a scope of an endoscope can be very easily stored within an elongated cleaning vessel of the endoscope cleaning apparatus under the vertically suspended condition, and can be sufficiently cleaned by forcibly applying the cleaning fluid to the surface of the scope. Since the position where the endoscope cleaning apparatus according to the invention is located has the specific relationship with the position where the used scope is suspended in view of the scope cleaning operation, the used scope can be very simply cleaned, which is comparable to the above-described manual cleaning operation where the used scope suspended on the scope stand is manually wiped by the gauze wetted by the cleaning fluid.

BRIEF DESCRIPTION OF THE DRAWINGS

The invention is best understood by studying the specification in conjunction with the accompanying drawings; in which;

FIG. 4 is a schematic sectional view of the endoscope cleaning apparatus shown in FIG. 3;

FIG. 5 is a schematic sectional view of an endoscope cleaning apparatus according to a second preferred embodiment of the invention;

DETAILED DESCRIPTION OF THE PREFERRED EMBODIMENTS

General Description

Figure 1:
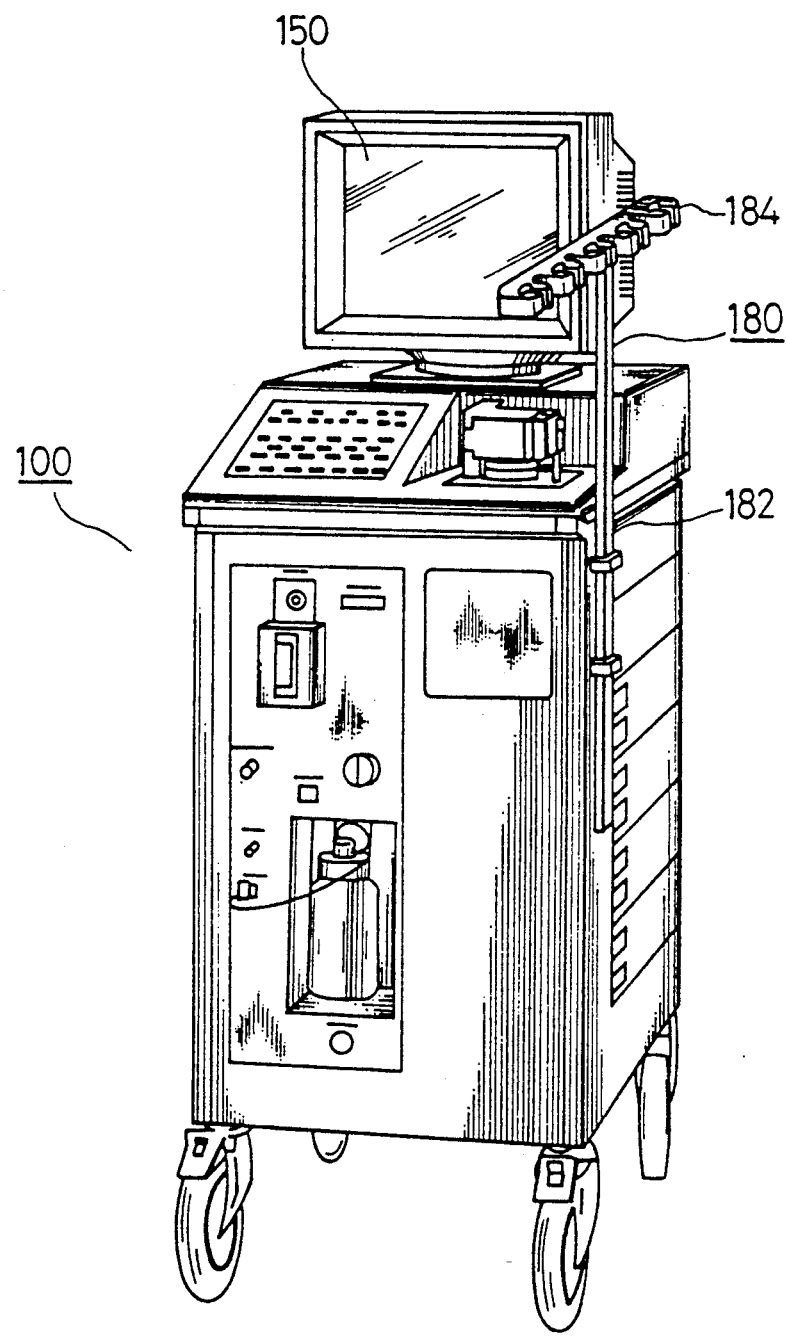
FIG. 1 is an illustration of an endoscope apparatus equipped with an endoscope stand to which an endoscope cleaning apparatus according to the present invention is attached.

Referring now to FIG. 1, an overall endoscope apparatus 100 equipped with a scope stand 180 to which an endoscope cleaning apparatus (will be discussed later), according to the present invention, is adapted, will be described.

Figure 2:
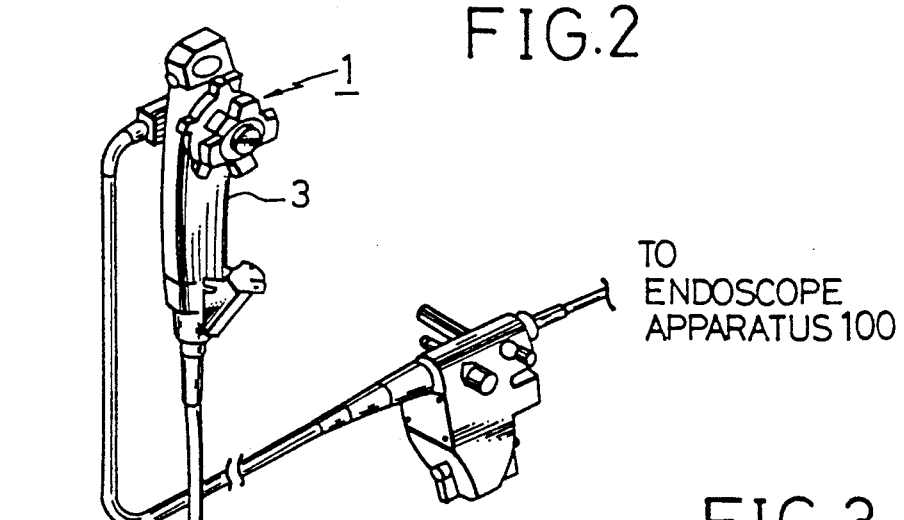
FIG. 2 is an illustration of an endoscope connectable to the endoscope apparatus shown in FIG. 1.

In FIG. 1, a monitor unit 150 is mounted on an upper portion of the endoscope cleaning apparatus 100. The scope stand 180 is attached to a left side wall of the endoscope apparatus 100. This scope stand 180 is constructed of an expansion rod 182 and a scope holder 184. The expansion rod 182 is of a telescopic rod. A scope 2 of an endoscope 1, as shown in FIG. 2, can be suspended by the scope holder 184 in such a manner that a distal end of the scope 2 is first inserted into a receiving end of the scope holder 184 and thereafter an operation unit 3 thereof is suspended by this receiving end. An endoscope cleaning apparatus according to the invention is attached to a proper position of an upper portion of this expansion rod 182 (will be discussed later).

The endoscope cleaning apparatus is used to clean the entire scope (insertable portion) 2 of the endoscope 1 shown in FIG. 2. This insertion section 2 of the endoscope 1 is made of, for instance, a fiber scope which is inserted into a biological body. In general, a typical length of a scope (insertion portion) of an endoscope is approximately 1 to 1.5 meters. Accordingly, a length of the endoscope cleaning apparatus 20 in a longitudinal direction thereof is substantially equal to, or longer than the typical length of the insertion portion of the scope.

Fluid Injection Type Cleaning Apparatus

Figure 3:
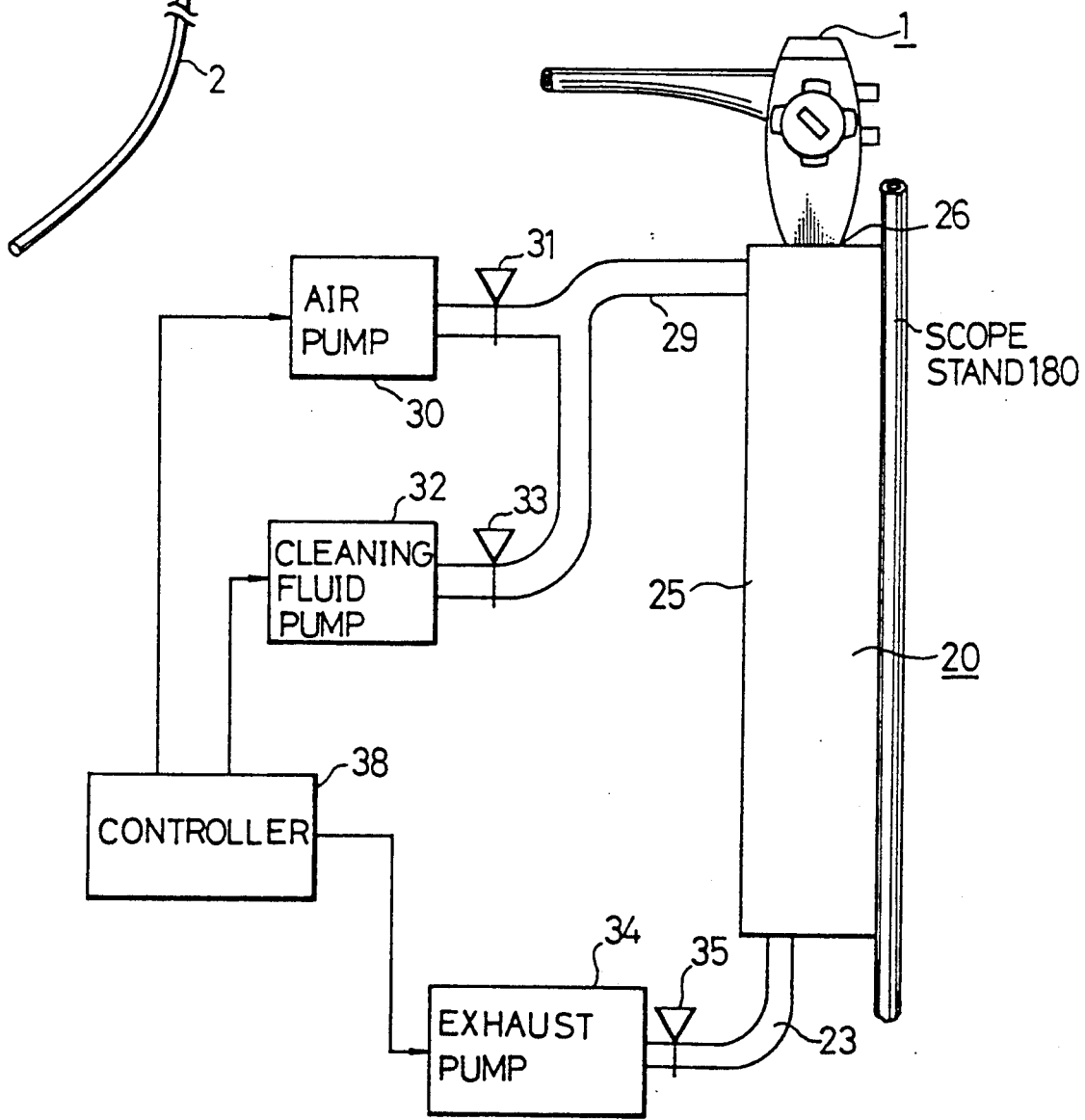
FIG. 3 illustrates an endoscope cleaning apparatus according to a first preferred embodiment of the invention, and peripheral apparatus thereof.

In FIGS. 3 and 4, there is shown a fluid injection type cleaning apparatus 20 suspendable by the scope stand 180, according to a first preferred embodiment of the invention.

FIG. 3 is a schematic diagram of the fluid injection type cleaning apparatus 20 and a peripheral apparatus. FIG. 4 is a cross-sectional view of a major portion of the fluid injection type cleaning apparatus 20

The fluid injection type cleaning apparatus 20 shown in FIG. 3 is used to clean the entire surface of the scope 2 of the endoscope 1, as illustrated in FIG. 2. As clearly shown in FIG. 3, the fluid injection type endoscope cleaning apparatus 20 is detachably mounted on the expansion rod 182 of the endoscope stand 180. The fluid injection type endoscope cleaning apparatus 20 is mainly constructed of a cylindrical vessel 25, an endoscope insertion hole 26, and a cylindrical injection body 27. A length of the cylindrical vessel 25 is so designed as to entirely store the entire insertion portion of the scope 2 under the condition that the endoscope 1 is suspended as shown in FIG. 3. In other words, since the typical endoscope employs the scope 2 having a length from 1 to 1.5 meters, the length of the cylindrical vessel 25 is substantially equal to, or longer than that of the scope length.

As illustrated in FIG. 4, the cylindrical injection body 27 is provided along the inside wall of the cylindrical vessel 25. A plurality of air/cleaning fluid injection holes 27A are formed in the cylindrical injection body 27 along a longitudinal direction. Alternatively, a plurality of injection nozzles may be formed on the cylindrical injection body 27. As will be discussed later, either cleaning fluid or drying air is injected through these injection holes 27A to the entire scope 2 of the endoscope 1.

Referring back to FIG. 3, the peripheral apparatus of the fluid injection type endoscope cleaning apparatus 20 will now be described in detail.

One end of a fluid/air supply tube 29 is connected to the left upper portion of the cylindrical vessel 25. Another end of the fluid/air supply tube 29 is connected via an air valve 31 to an air pump 30, whereas another end thereof is connected via a first fluid valve 33 to a cleaning fluid pump 32. One end of an exhaust tube 23 is connected to the bottom of the cylindrical vessel 25. The other end of the exhaust tube 23 is connected via a second fluid valve 35 to a pump 34. These three different pumps 30, 32 and 34 are under control of the sequential control method.

During the cleaning operation, the scope 2 of the endoscope 1 is first suspended by the scope stand 180 detachably connected to the cylindrical vessel 25. To suspend the scope 2 of the endoscope 1, the distal end of the scope 2 is first inserted through the scope insertion hole 26 of the cylindrical vessel 25, and thereafter the operation unit 3 of the endoscope 2 shuts this scope insertion hole 26.

Under the above-described conditions, the entire scope 2 of the endoscope 1 can be cleaned within the cylindrical vessel 25 as follows.

During the cleaning operation, the cleaning fluid composed, e.g., water, a cleaning fluid, and a soap fluid is first supplied from the cleaning fluid pump 32 via the first fluid valve 33 (being opened) and the fluid supply tube 29 into the cylindrical injection body 27 positioned in the cylindrical vessel 25. When the supply of the cleaning fluid is commenced, then the cleaning operation for the scope 2 stored within the cylindrical vessel 25 starts substantially simultaneously. That is, the cleaning fluid is injected from the injection holes 27A of the injection body 27 toward the overall surface of the scope 2. An effluent caused by the cleaning operation of this cleaning fluid is forcebly drawn via the exhaust tube 23 and the second fluid valve (being opened) 35 by the exhaust pump 34.

In particular, when the soap fluid is used as this cleaning fluid, water is additionally supplied from the cleaning fluid pump 32 into the injection body 27 after completion of the cleaning operation by utilizing the soap fluid so as to achieve the perfect cleaning operation.

After the cleaning operation by use of the cleaning fluid is accomplished, the first fluid valve 33 and second fluid value 35 are closed under the control of the controller 38 and thereafter the air valve 31 is opened and also the air pump 30 is energized under the control of the controller 38. The air is supplied from the air pump 30 via the air valve 31 and fluid/air supply tube 29 to the injection body 27 provided within the cylindrical vessel 25. Thus, the air is injected through the injection holes 27A of the injection body 27 toward the entire surface of of the scope 2 stored within this cylindrical injection body 27. As a result, the wetted surface of this scope 2 is dried by this injection air.

When the drying operation is completed, the cleaned and dried scope 2 of the endoscope 1 is picked up. Thus, the cleaned scope 2 of the endoscope 1 can be immediately prepared for the medical endoscope inspection.

Moving Blade Type Cleaning Apparatus

Referring now to a sectional view of FIG. 5, a moving blade type cleaning apparatus 40 according to a second preferred embodiment of the invention will be described. It should be noted that the same reference numerals will be employed for denoting the same or similar components shown in FIGS. 3 and 4, and also since peripheral apparatus for this type of cleaning apparatus 40 are the same as those of the first preferred embodiment, no further explanation will be made.

As clearly illustrated in FIG. 5, in an upper portion of the cylindrical vessel 25 of the moving blade type cleaning apparatus 40, similarly the scope insertion hole 26 is formed. The effluent exhaust tube 23 is connected to the bottom of the cylindrical vessel 25. A moving blade 48 is mounted on a different portion of the bottom. The blade 48 is rotatably driven by a blade driver 44. The blade driver 44 is connected to the controller 38 shown in FIG. 3.

During the cleaning operation of this moving blade type endoscope cleaning apparatus 40, after the cleaning fluid is begun to be supplied from the cleaning fluid pump 32 via the first fluid valve 31 (being opened) and tube 29 into the interior of the cylindrical vessel 25 of the endoscope cleaning apparatus 40, the moving blade 48 is rotated by the blade driver 44 in the similar manner as the usual washing machine when a predetermined quantity of the cleaning fluid is stored within the cylindrical vessel 25. As a consequence, a vortex line is produced by rotating the moving blade 48 to establish the rotation of the cleaning fluid, so that the entire scope 2 of the endoscope 1 stored within the cylindrical vessel 25 can be cleaned by the cleaning fluid. After the completion of the cleaning operation, the second fluid valve 35 is opened to conduct the effluent of the cleaning fluid via the exhaust tube 34 to the exhaust pump 34. When the effluent exhaust operation is completed, this second fluid valve 35 is again closed. In case of using the soap fluid, water is conducted within the cylindrical vessel 25 for the cleaning purpose. As a result, the cleaning operation by the cleaning fluid for the surface of the scope 2 of the endoscope 1 can be accomplished.

Thereafter, the air valve 31 is opened and the first fluid valve 33 is closed, and then the air pump 30 is turned on. The air is supplied from the air pump 30 into the cylindrical vessel 25 so as to dry the cleaned surface of the scope 2 of the endoscope 1.

Moving Brush Type Cleaning Apparatus

Figure 6:
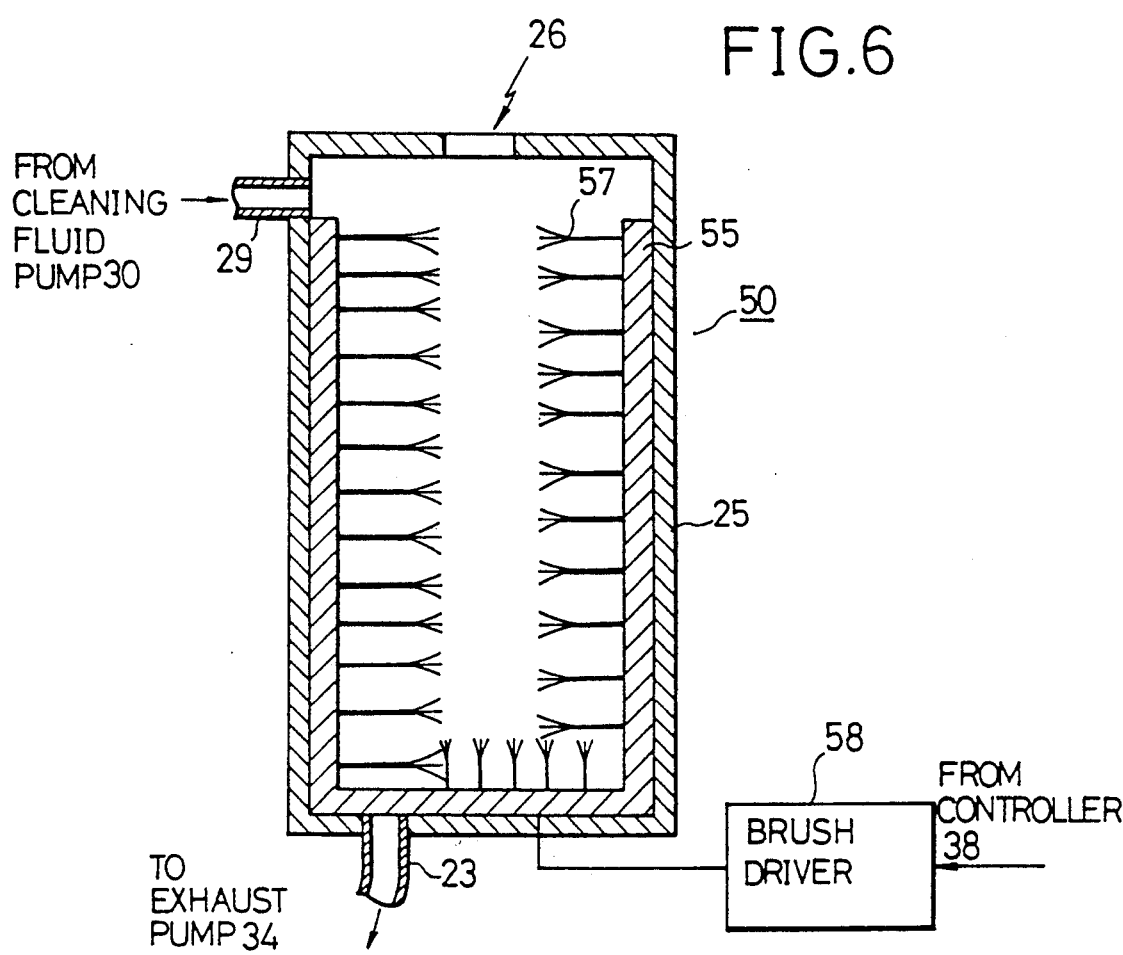
FIG. 6 is a schematic sectional view of an endoscope cleaning apparatus according to a third preferred embodiment of the invention; and, FIG. 7 to 10 are illustration of endoscope cleaning apparatuses according to fourth to seventh preferred embodiments of the invention.

FIG. 6 is a cross-sectional view of a moving brush type cleaning apparatus 50 according to a third preferred embodiment of the invention.

As is apparent from FIG. 6, a rotary cylinder 55 is positioned within the cylindrical vessel 25. Brushes 57 are planted on the inside wall of the rotary cylinder 55 in such a way that tip portions of the brushes 57 project toward a center of the rotary cylinder 55. This rotary cylinder 55, i.e., brushes 57 is driven by a brush driver 58 under the control of the controller 38 shown in FIG. 3.

The cleaning operation by the moving brush type cleaning apparatus 50 is similar to that of the above-described moving blade type endoscope cleaning apparatus 40. While the cleaning fluid is conducted into the inside of the rotary cylinder 55, the surface of the scope 2 is brushed by rotating the brushes 59 of the rotary cylinder 55 with respect to the longitudinal axis of the cleaning vessel 25.

Other Cleaning Apparatuses

Referring now to FIGS. 7 to 10, endoscope cleaning apparatus according to other preferred embodiments of the invention will be described briefly.

Figure 7:
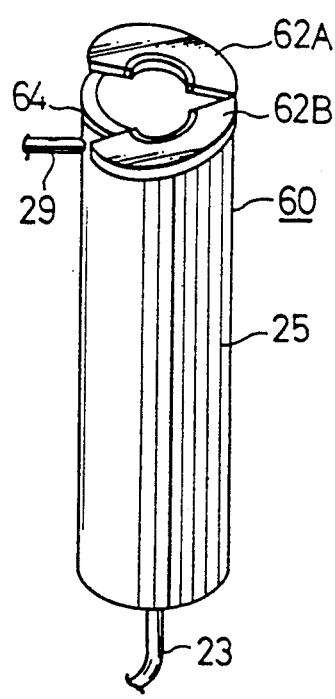

First, FIG. 7 illustrates an endoscope clearing apparatus 60 according to a fourth preferred embodiment of the invention. Top plate halves 62A and 62B of the cleaning apparatus 60 are made in air opening and closing movement. Accordingly, the upper portion of the cylindrical vessel 25 contactable with these top plate halves 62A and 62B is made of a water-proof material 64.

Figure 8:
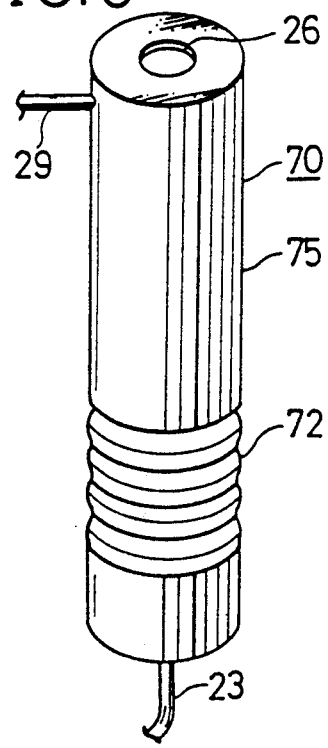

Secondly, FIG. 8 illustrates an endoscope cleaning apparatus 70 according to a fifth preferred embodiment of the invention. In this embodiment, an expansion part 72 is formed at the lower portion of the cylindrical vessel 75. As a consequence, depending upon the length of the scope 2 inserted into the cylindrical vessel 25, the length of the expansion part 72 is adjustable, which is a particular advantage of the fifth preferred embodiment.

Figure 9:
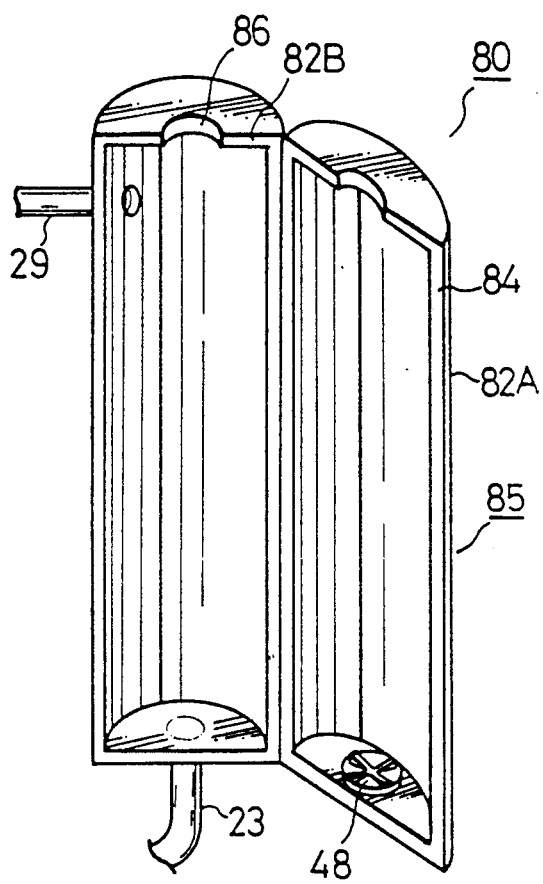

FIG. 9 illustrates an endoscope cleaning apparatus 80 according to a sixth preferred embodiment of the invention. According to the sixth endoscope cleaning apparatus 80, it is mainly constructed of a pair of semi-cylindrical vessel halves 82A and 82B. There is a particular advantage that the scope 2 can be easily stored within the cylindrical vessel 85 because of the dividable cylindrical vessel 85 along the longitudinal axis thereof. Similarly, the interiors of the cylindrical vessel halves 82A and 82B are made of a water-proof material 84. In this case, the scope insertion hole 86 is also made of the water-proof material.

Figure 10:
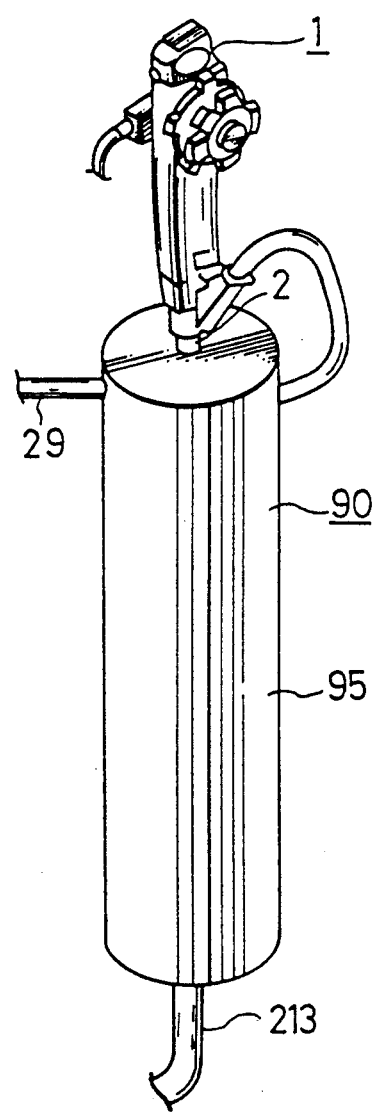

Furthermore, an endoscope cleaning apparatus 90 according to a seventh preferred embodiment of the invention is shown in FIG. 10.

As shown in FIG. 10, the cleaning operation of the scope 2 within a cylindrical vessel 95 is performed in conjunction with a cleaning mechanism (not shown in detail) for a channel of a forceps employed in this scope 2.

It is apparent that the present invention is not limited to the above-described endoscope cleaning apparatus, but may be realized in various modifications.

Instead of the rotation of the brushes 57 shown in FIG. 6, for instance the cylindrical vessel 25 may be reciprocated along its longitudinal axis, or may be twisted with respect to the longitudinal axis.

Also, a water-level sensor may be employed near the top portion of the cylindrical vessel 25 shown in FIG. 5, so as to sense that a predetermined quantity of the cleaning fluid is stored within the cylindrical vessel 25. Then,, a sensing signal is transferred from the water-level sensor to the controller 38 in order to turn off the cleaning fluid pump 32.

In addition, in the endoscope cleaning apparatus 80 shown in FIG. 8, a pressure sensor may be employed around the fixing portion of the cylindrical vessel halves 82A and 82B, so as to detect whether or not these cylindrical vessel halves 82A and 82B are tightly closed.

Furthermore, a drying mechanism may be additionally employed in the brush rotating mechanism 55 and 58.

In the above-described preferred embodiments, the cylindrical vessels were employed. Similarly, any vessels having shapes of a triangle, or rectangular, as viewed in a cross-sectional view thereof may be utilized. Eventually, any sort of vessels may be utilized if they can store the entire scope 2 under the vertically suspended condition, and clean the surface thereof, according to the invention.

In the above-described preferred embodiments, the cleaning apparatus, e.g., 20 were detachably attached to the extension rod 182 of the scope stand 180. Alternatively, these cleaning apparatus may be integrally formed with the extension rod 182.

Advantages of Cleaning Apparatus

While it has been described in detail, the endoscope cleaning apparatus according to the invention has the following particular advantages. That is, the entire scope of the endoscope can be stored under the vertically suspended condition within the cleaning vessel, and the cleaning fluid is forcebly applied to the overall surface of the scope for the cleaning purpose.

Since the endoscope cleaning apparatus is used in combination with the scope stand, the scope of the endoscope can be very simply cleaned while the endoscope inspection is performed, which is comparable to the conventional manual wiping cleaning operation during which the scope of the endoscbpe is suspended on the scope stand.

What is claimed is:

1. A cleaning apparatus for cleaning a scope of an endoscope insertable into a biological body under medical examination, comprising:

an elongated cleaning vessel including a top end portion and a bottom end portion positioned opposite to each other along a longitudinal axis thereof, a scope insertion hole formed in said top end portion, through which said scope of the endoscope is insertable, whereby a substantially entire length of said scope is stored within said elongated cleaning vessel in a vertical direction parallel to said longitudinal axis, a cleaning-fluid conducting hole formed in a first portion adjacent to said top end portion, through which cleaning fluid is conducted into said elongated cleaning vessel, and, an exhaust hole formed in a second portion adjacent to said bottom end portion, through which effluent of the cleaning fluid is exhausted form the elongated cleaning vessel, said elongated cleaning vessel being constructed of a pair of semi-cylindrical vessel halves extending along the longitudinal axis thereof, and said semi-cylindrical vessel halves being hinged with each other so as to be opened for allowing said scope to be inserted into said cleaning vessel.

2. A cleaning apparatus as claimed in claim 1, wherein each of said semi-cylindrical vessel halves has a substantially half insertion hole portion on said top portion thereof, whereby said scope inserted into said cylindrical vessel halves is firmly positioned on said insertion portions.

3. A cleaning apparatus as claimed in claim 1, wherein said pair of semi-cylindrical vessel halves are made of a water-proof material.

4. A cleaning apparatus as in claim 1, further comprising a rotatable blade mounted on an inner surface of the bottom end portion of one of said vessel halves.

* * * * *